(12) United States Patent
Clarke et al.

(10) Patent No.: US 8,196,774 B1
(45) Date of Patent: Jun. 12, 2012

(54) REMOTE PHARMACEUTICAL DISPENSING

(75) Inventors: Darcy O. Clarke, Kent, WA (US);
James E. Torina, Issaquah, WA (US)

(73) Assignee: Talyst Inc., Bellevue, WA (US)

( * ) Notice: Subject to any disclaimer, the term of this patent is extended or adjusted under 35 U.S.C. 154(b) by 314 days.

(21) Appl. No.: 12/360,060

(22) Filed: Jan. 26, 2009
(Under 37 CFR 1.47)

Related U.S. Application Data

(60) Provisional application No. 61/023,386, filed on Jan. 24, 2008.

(51) Int. Cl.
*B65H 1/00* (2006.01)
(52) U.S. Cl. .............. 221/197; 221/13; 221/30; 221/70; 221/89; 221/154
(58) Field of Classification Search .................... 221/13, 221/30, 70, 89, 154, 197
See application file for complete search history.

(56) References Cited

U.S. PATENT DOCUMENTS

| | | | | |
|---|---|---|---|---|
| 3,131,830 A | * | 5/1964 | Schaef | 221/25 |
| 3,964,638 A | * | 6/1976 | Dimauro | 221/3 |
| 4,674,652 A | * | 6/1987 | Aten et al. | 700/236 |
| 4,823,982 A | * | 4/1989 | Aten et al. | 221/3 |
| 5,102,008 A | * | 4/1992 | Kaufman et al. | 221/25 |
| 5,963,136 A | | 10/1999 | O'Brien | |
| 6,394,306 B1 | * | 5/2002 | Pawlo et al. | 221/2 |
| 6,611,733 B1 | * | 8/2003 | De La Huerga | 700/236 |
| 6,961,285 B2 | | 11/2005 | Niemiec | |
| 6,962,266 B2 | * | 11/2005 | Morgan et al. | 221/25 |
| 7,002,476 B2 | | 2/2006 | Rapchak | |
| 7,080,755 B2 | * | 7/2006 | Handfield et al. | 221/9 |
| 7,963,201 B2 | * | 6/2011 | Willoughby et al. | 221/25 |
| 2005/0049747 A1 | | 3/2005 | Willoughby | |

* cited by examiner

*Primary Examiner* — Timothy Waggoner
(74) *Attorney, Agent, or Firm* — Christensen O'Connor Johnson Kindness PLLC (57) ABSTRACT

A remote pharmaceutical dispensing system for automatically dispensing medication includes a plurality of packets each containing at least one type of medication for a predetermined hour of administration (HOA). The system also includes at least one cartridge having a housing and a feed mechanism disposed within the housing for advancing at least one of the plurality of packets toward an opening in the cartridge housing. The system further includes a dispenser having a dispenser housing configured to receive the at least one cartridge and a motor that is drivably engageable with the feed mechanism of the cartridge when the cartridge is inserted into the dispenser. The system also includes a controller in operable communication with the motor and configured to actuate the motor to advance at least one of the plurality of packets toward an opening in the dispenser housing at the predetermined HOA.

12 Claims, 6 Drawing Sheets

REMOTE PHARMACEUTICAL DISPENSING

CROSS-REFERENCE TO RELATED APPLICATION

This application claims priority to U.S. Provisional Patent Application No. 61/023,386, filed on Jan. 24, 2008, the disclosure of which is hereby expressly incorporated by reference.

BACKGROUND

As it relates to the Home Care markets, medication compliance is recognized as a major problem in healthcare today. Typically there is no 'staff' and little assistance for the 'home patient' in managing multiple prescriptions, inventories, and change. The average senior person is prescribed on the order of thirteen different oral medications that must be taken correctly each day. These medications are typically delivered in bulk supply and must be sorted/managed and taken correctly by the individual, leading to numerous errors and omissions, including misusing the medications, taking the medications at the wrong time and/or in the incorrect amount, failing to take the medications at the prescribed time, fatally combining the medications with other medications, under-using the medications, over-using the medications, etc.

The costs associated with such non-compliance are more serious than a number of major illnesses combined. Studies have provided the following facts:

- 10% of admissions to regular hospitals are due to non-compliance, at a cost of $15 billion a year
- 30% of hospital admissions for people over the age of 65 are directly caused by non-compliance
- Non-compliance causes 125,000 deaths a year—twice as many as auto accidents;
- 23 to 40% of nursing home admissions are due to noncompliance, inability to take medications at home unsupervised
- Half of all prescriptions are taken incorrectly, contributing to prolonged or additional illness
- People who miss doses need 3 times as many doctor visits as other and face an average of $2,000 more in medical costs per year The fact that the aging population continues to grow combined with the steady increase in the average number of medications prescribed per person indicates that these issues will continue to compound along with the associated costs. Thus, it is clear that a system that automatically dispenses medications to the home patient at the correct time and that further monitors the medication dispensing and reacts in a predetermined manner to a missed medication is needed. Moreover, since the majority of home patients will be taking more than one type of medication at more than one prescribed time, or "hour of administration" (HOA) each day, the system should also be able to easily accept and dispense multiple types of medication and dispense different doses of medication throughout the day.

Furthermore, it is also important that such a system be easy to use. Many home patients are senior persons or persons having disabling illnesses that may not have the ability, strength, or awareness to easily set up and use the system. For instance, a home patient would likely have difficulty loading medications into a dispensing system that has a complicated feed mechanism for dispensing the medications. This would likely deter the home patient from using such a system without the assistance of a nurse or other caregiver. As stated above, there is typically no staff and little assistance for the home patient in complying with medication plans. Thus, it is desirous to provide a system for automatically tracking and dispensing medications in a remote location that is easy to use.

SUMMARY

A remote pharmaceutical dispensing system for automatically dispensing medication is provided. The remote pharmaceutical dispensing system includes a plurality of packets each containing at least one type of medication for a predetermined hour of administration, and at least one cartridge having a cartridge housing and a feed mechanism disposed within the cartridge housing. The feed mechanism is suitable for advancing at least one of the plurality of packets toward an opening in the cartridge housing. The system further includes a dispenser having a dispenser housing sized and configured to receive the at least one cartridge and an opening in substantial alignment with the opening in the cartridge housing. The dispenser further includes a motor that is drivably engageable with the feed mechanism of the cartridge when the cartridge is inserted into the dispenser. The system also includes a controller in operable communication with the motor and configured to actuate the motor to advance at least one of the plurality of packets toward the opening in the dispenser housing at the predetermined hour of administration.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 1:
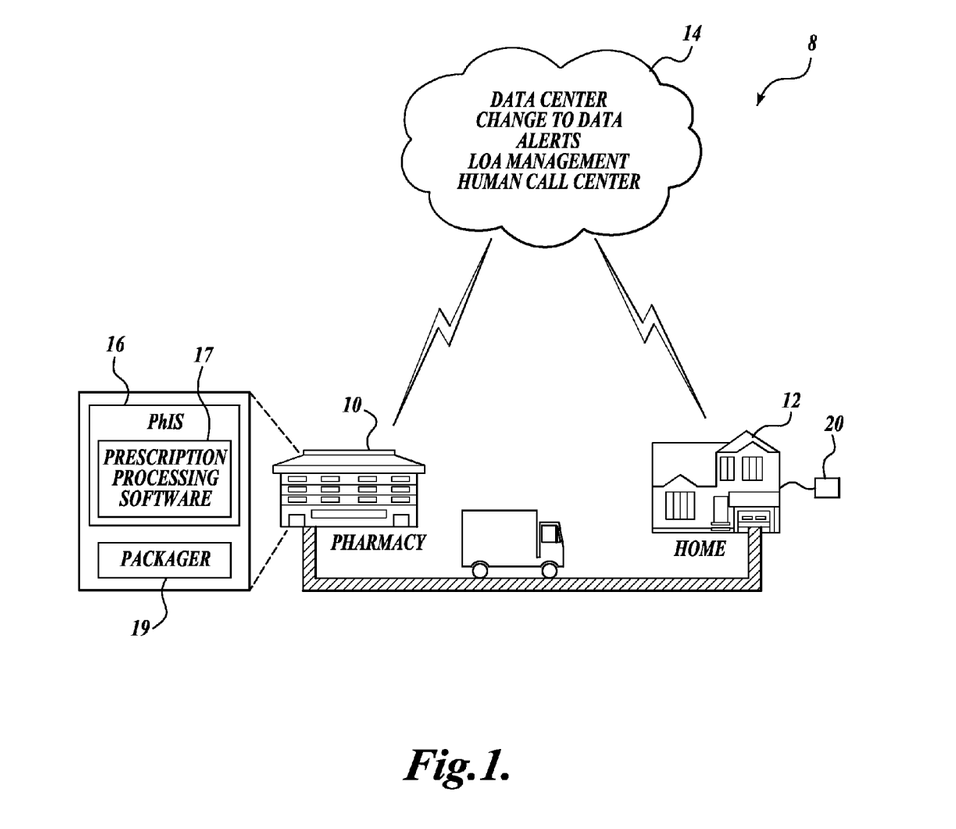
FIG. 1 is a graphical depiction of a remote pharmaceutical dispensing system formed in accordance with a preferred embodiment of the present disclosure.

Referring to FIG. 1, a remote pharmaceutical dispensing system 8 constructed in accordance with one embodiment of the present disclosure is provided. The remote pharmaceutical dispensing system 8 includes a pharmacy 10 or other medication supplier/distributor that is capable of receiving and packaging prescriptions in any suitable manner. The packaged prescriptions are sent to a person's home 12 or other remote location for automatic dispensing from a dispenser 20

Figure 5:
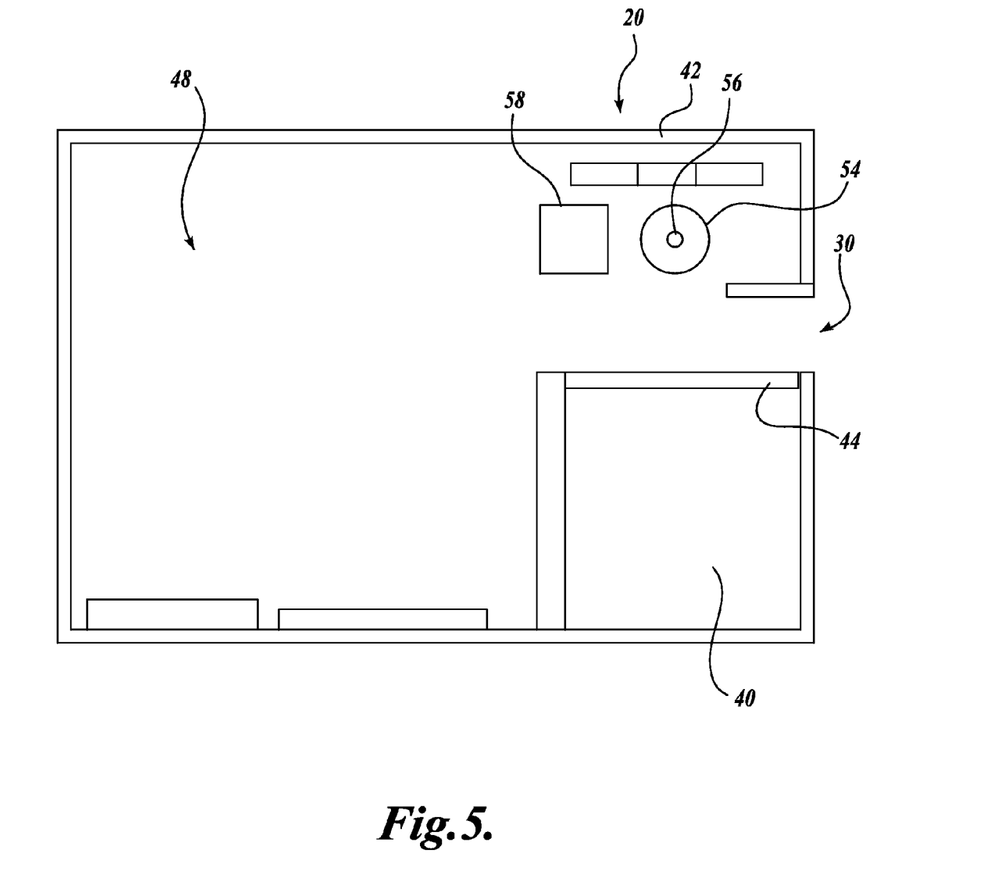
FIG. 5 is an isometric view of a dispenser of the remote pharmaceutical dispensing system of FIG. 1, wherein the dispenser is shown in a first position.
Figure 6:
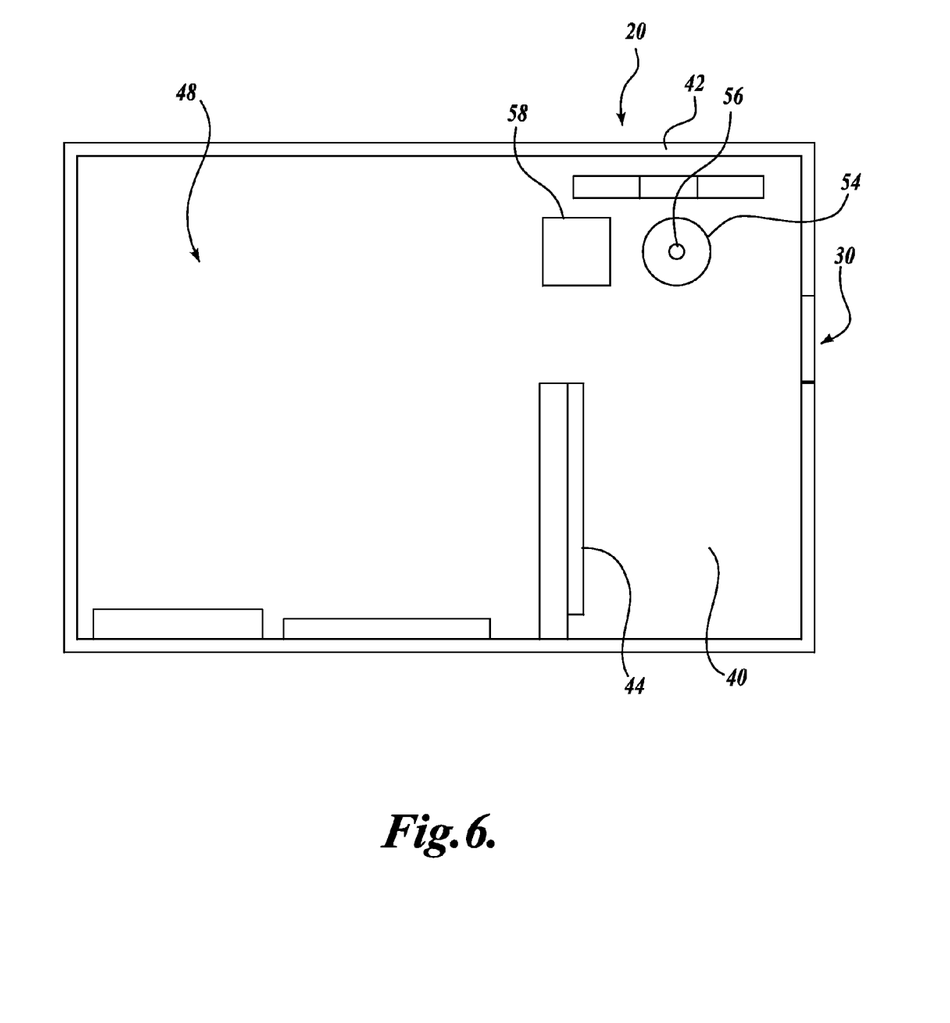
FIG. 6 is an isometric view of the dispenser of FIG. 5 shown in a second position.

(see also FIGS. 5 and 6). Both of the pharmacy 10 and the dispenser 20 are in networked communication with a data center 14. The data center 14 is the centralized controlling network of the remote pharmaceutical dispensing system 8. The data center 14 receives instructions from the pharmacy 10 and communicates with the dispenser 20 for instructing the dispenser 20 to dispense the medications and for monitoring the dispensing activities. It should be appreciated that the pharmacy 10 and the data center 14 may also be in communication with numerous other dispensers 20 located at various other remote locations. Moreover, the data center 14 may also be in communication with hospitals, caregivers, doctors, or other third parties for carrying out emergency response protocols in the event that the system fails or in the event that a patient fails to correctly take his or her medication. However, the system 8 will be hereinafter described as having only a pharmacy 10, a data center 14, and a single dispenser 20 for ease of description and illustration.

The pharmacy 10 includes a pharmacy information system 16 or "PhIS" having software 17 that is capable of receiving and processing prescriptions for each patient in any suitable manner. The prescriptions are sent to the pharmacy 10 from the data center 14 (or any other data source) or from a request originated through the patient. The prescription is entered into the pharmacy information system 16, and each prescription is saved to a file that also includes other prescriptions for the patient. The pharmacy information system 16 processes each prescription by creating a batch file that divides the prescription into single line orders. For example, if a patient has a prescription for two pills to be taken twice a day for ten days, the pharmacy software 17 will create twenty lines of orders. Each line order will request a quantity of two pills to be packaged in a packet, and each packet is assigned an hour of administration (HOA). The HOA is the time at which the medications are to be taken. For example, the HOA may be "Breakfast" or "08:00." Each order is also grouped with other medication orders (if received) having the same HOA to allow for the creation of multi-dose HOA packets during the packaging process.

Upon receiving and processing the prescriptions, the pharmacy 10 packages each of the prescriptions into single or multi-dose packets for each HOA for a predetermined period of time, such as one week, ten days, one month, etc. The supplying pharmacy 10 is preferably equipped with automated packaging equipment that is capable of automatically packaging the patient's required medications into single or multi-dose packets upon manual or automatic command from the pharmacy information system 16. However, it should be appreciated that the pharmacy 10 may instead cooperate with a third party for packaging/distributing the medications. Preferably, the pharmacy 10 or third party includes an automated high-speed packager 19, such as the Talyst AutoPack™, available from Talyst, Inc., of Bellevue, Wash., for filling and packaging a patient's prescriptions into the packets. However, any suitable automatic or manual packaging system may instead be used.

Each packet contains all the medications that are required for the patient to take at the predetermined HOA. If the patient requires more medications for an HOA than can be safely stored in one packet, the remaining medications for the HOA are packaged in the next packet and the packets are labeled as "1 of 2" and "2 of 2" with instructional text on the packets to direct the patient to take both packets.

The pharmacy 10 also creates an electronic manifest that is a record of all medication packets, their contents, the dispensing schedule (HOA), the patient's name, and any other required patient information for the packages. This manifest is sent electronically to the dispenser 20 through the data center 14 prior to the medications being sent to the user. The data center 14 routes the information contained in each electronic manifest to the correct dispenser 20. The manifest is sent via secured messaging over a secured Wide Area Network that is controlled by the data center 14. Central control of information passing between the pharmacy 10 and the dispenser 20 permits supervision and management of data, alerts, leave of absence (LOA) notices, inventory levels, and other information. Moreover, information received from the dispenser 20, such as alarms, refill requests, and dispensing activity indicators are managed, processed, and/or distributed to the correct destinations by the data center 14. All electronic data exchanges that occur between the pharmacy 10, the data center 14, and the dispenser 20 occur over a secure network. A human call center can also respond to either patient or pharmacy problems in addition to the data center 14.

Figure 2:
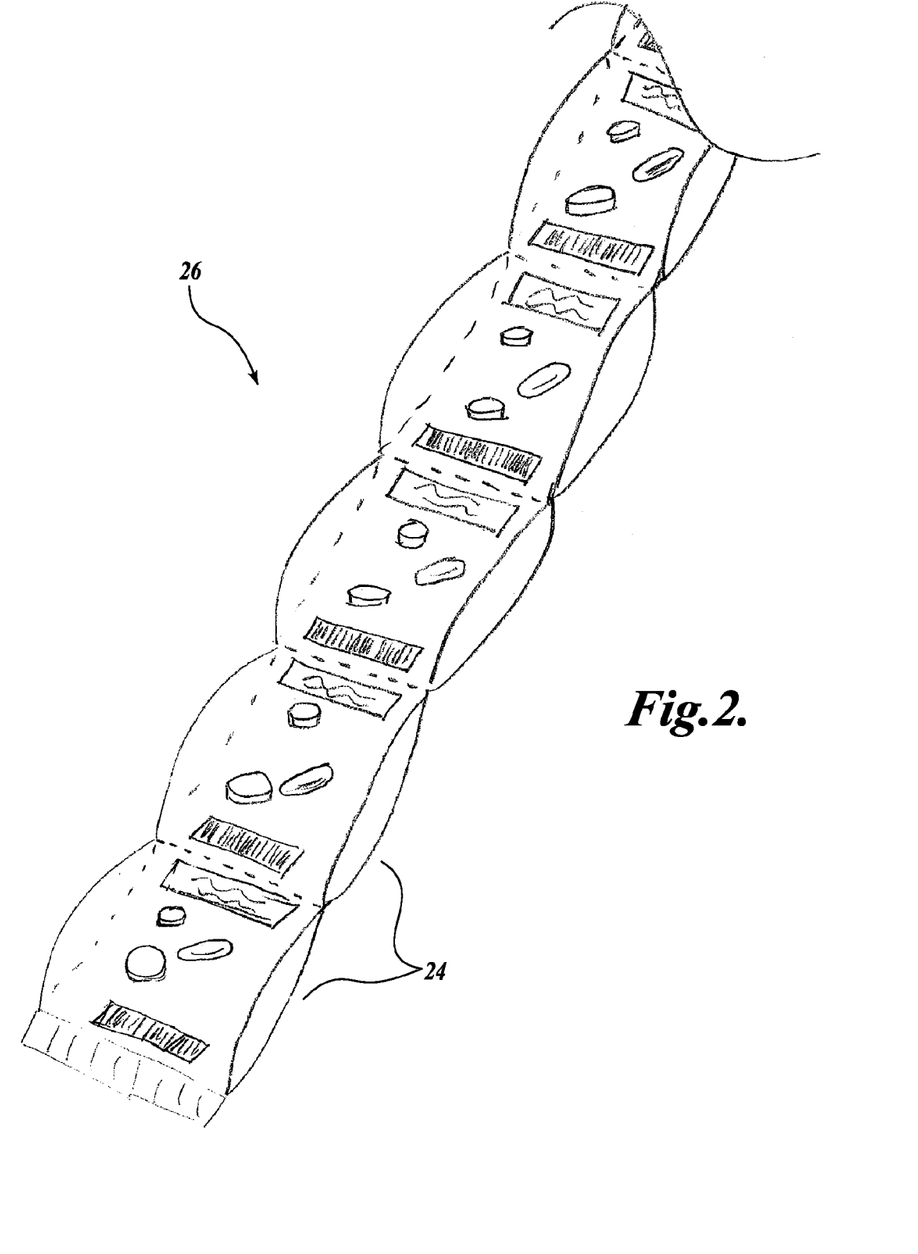
FIG. 2 is an isometric view of a plurality of medication packets for use with the remote pharmaceutical dispensing system.

Referring to FIG. 2, all the patients' medications for a specific HOA (such as 8:00 AM) are packaged into individual HOA dose packets 24 (or multiple packets if needed) and are connected together to form a medication HOA strip 26 for a predetermined amount of time, such as ten days. In other words, the HOA strip 26 is comprised of the predetermined number of individual HOA dose packets 24 sufficient to provide each HOA dose for the predetermined period of time. The individual HOA dose packets 24 are separated along the HOA strip 26 by a transverse perforation that allows for easy separation of the HOA strip 26 into the individual HOA dose packets 24. The HOA dose packets 24/HOA strip 26 can be made from any suitable material, such as a cellophane film, and the HOA dose packets 24 can be of any size to properly accommodate medications. The packets are preferably made of cellophane film and are about 75 mm by 70 mm in size. This preferred size and style of packaging is well-known with the industry and is commercially available today from several manufacturers around the world. The HOA dose packets 24 are labeled with any suitable information, such as the packet contents, instructions for taking the medication, etc. The HOA dose packets 24 may also include a bar code, RFID tag, colors, symbols, etc. for identifying the packet. It should be appreciated that the HOA dose packets 24 may instead be configured in a form other than a strip that allows for serial dispensing of the packets.

Figure 3:
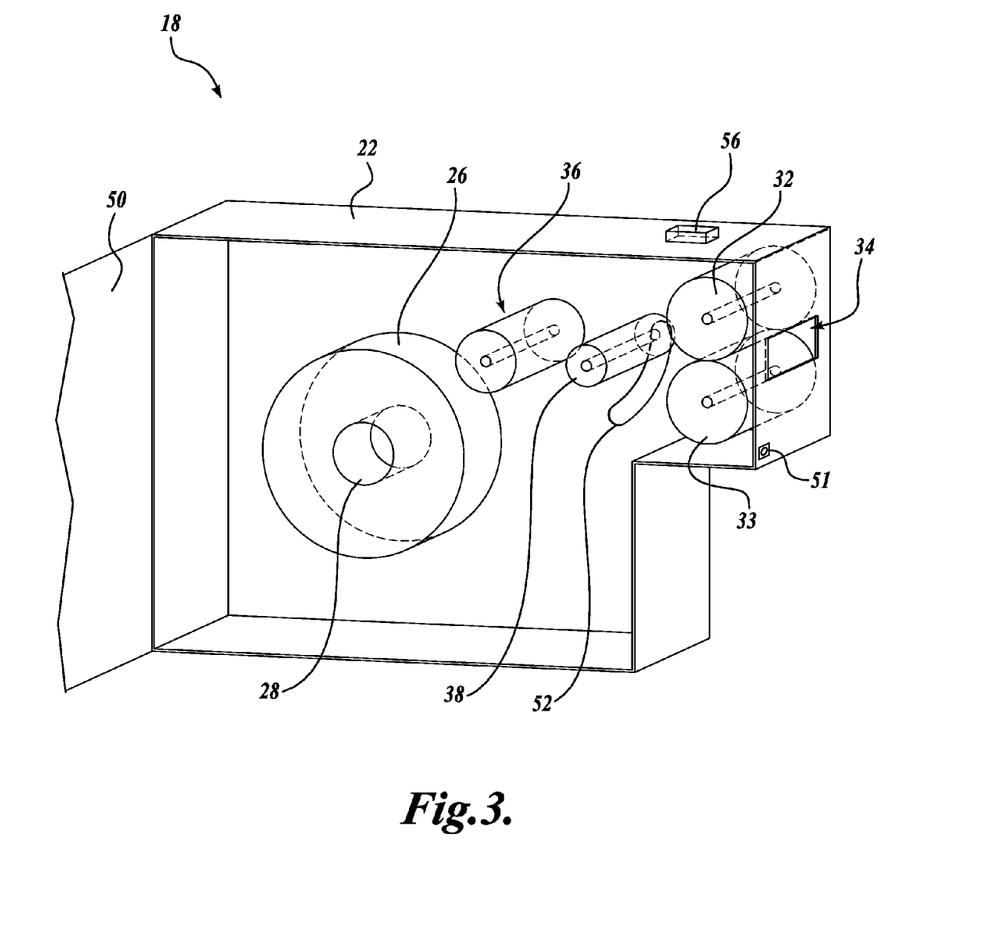
FIG. 3 is an isometric view of a dispensing cartridge of the remote pharmaceutical dispensing system of FIG. 1.
Figure 4:
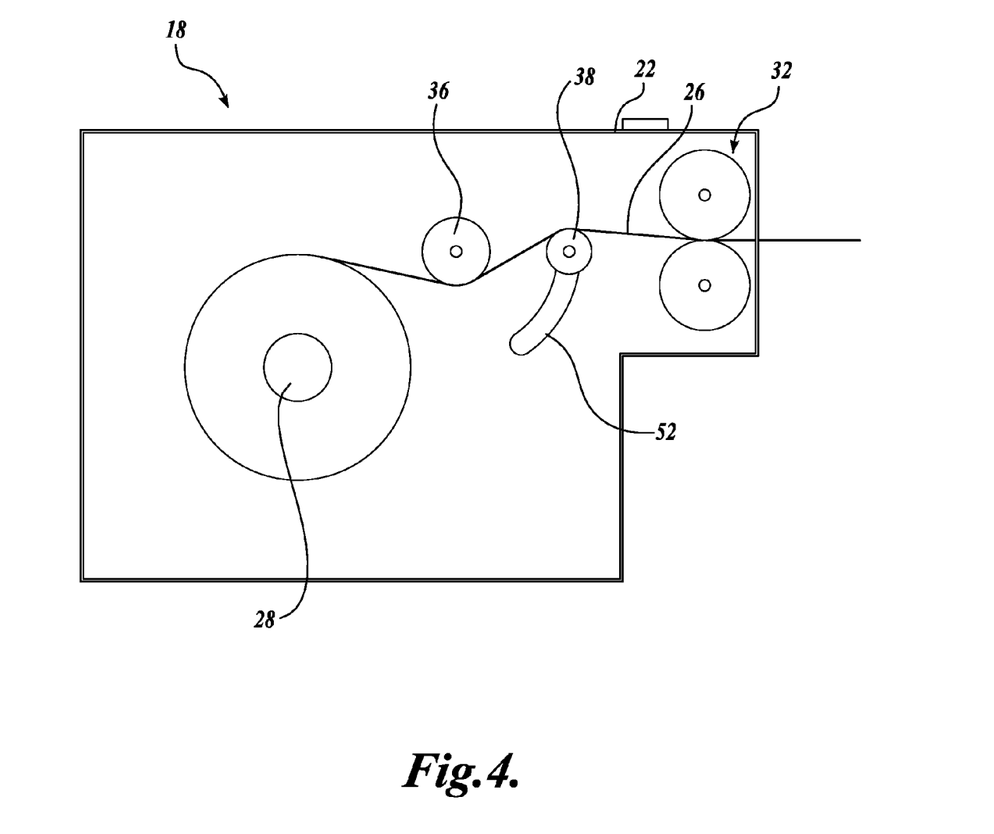
FIG. 4 is a side view of the dispensing cartridge of FIG. 2 shown dispensing a plurality of packets.

Referring to FIGS. 3 and 4, after the medications are packaged into the HOA dose packets 24 to define an HOA strip 26, the pharmacy 10 or third party supplier/distributor loads each HOA strip 26 into a designated dispensing cartridge 18 that is sized and configured for use with the dispenser 20 located in the patient's home 12. The dispensing cartridge 18 is a secure device that provides child safe, tamper evident protection for the HOA dose packets 24 during the shipping and dispensing process. Each dispensing cartridge 18 is loaded with a single HOA strip 26 of HOA dose packets 24 for the predetermined time frame (i.e. 10 days).

The dispensing cartridge 18 further includes a globally unique identifier (GUI) 56, RFID tag, or other suitable device for identifying the dispensing cartridge 18 when inserted into the dispenser 20. The GUI for each dispenser 18 is communicated to the date center 14 from the pharmacy 10 in the electronic manifest. The dispenser 20 communicates with the data center 14 to identify the cartridge 18 by the GUI 56. Upon identifying the cartridge 18, the data center 14 can relay dispensing instructions to the dispenser 20 for each cartridge 18. As such, the dispenser 20 will automatically dispense the HOA dose packets 24 for each cartridge 18 at the appropriate HOA.

The dispensing cartridge 18 is of a suitable design such that it is ready for automatic dispensing upon insertion into the dispenser 20. The dispensing cartridge 18 preferably includes a housing 22 that encloses a feed mechanism for receiving an HOA strip 26 and feeding the HOA strip 26 towards an opening 34 in the housing 22 when it is the appropriate HOA. The housing 22 preferably includes a hinged door or cover 50 or other suitable device for selectively accessing the interior of the housing 22 and securing the contents of the housing 22 for shipping and dispensing. A suitable lock 51 or other device may be also used to secure the contents of the housing 22.

A main roller 28 is journaled for rotation within the cartridge housing 22 and is adapted to receive a rolled HOA strip 26 thereon. The HOA strip 26 may be disposed on a hollow cylindrical member or post, or may instead be directly rolled onto the main roller 28. If the HOA strip 26 is disposed onto a hollow cylindrical member, the main roller 28 may be sized to define a friction fit therebetween or may instead include another suitable mechanism for removably securing the HOA strip 26 onto the main roller, such as a ball detent mechanism or a snap fit device. Moreover, the HOA strip 26 may instead be received on a main feed roller that is removably securable within the housing 22. It should be appreciated that the HOA strip 26 may instead be disposed within the housing 22 of the dispensing cartridge 18 in any suitable manner. For instance, the housing 22 may instead include an internal compartment that receives the HOA strip 26 in a folded, accordion-like fashion.

A pair of feed rollers 32 and 33 are also journaled for rotation within the housing 22 near the opening 34, wherein the axis of rotation for each feed roller 32 and 33 is in substantial parallel alignment. Moreover, the feed rollers 32 and 33 are positioned adjacent to one another and spaced apart a predetermined distance such that the HOA strip 26 may be received therebetween to advance the HOA strip 26 toward the opening 34. It is preferred that the HOA strip 26 be tightly received between the feed rollers 32 and 33 such that the HOA strip 26 be frictionally engaged by the feed rollers 32 and 33 and easily advanced toward the opening 34. However, it is also preferred the feed rollers 32 and 33 be sufficiently spaced or be made of a sufficiently pliant material such that the medications within the HOA packets 24 are not crushed or otherwise damaged during the dispensing process. The feed rollers 32 and 33 may instead include protrusions that are engageable with openings formed in the HOA strip 26 for advancing the HOA strip toward the opening 34. Moreover, any other suitable feed mechanism may instead be used without departing from the spirit and scope of the present disclosure.

The main roller 28 and/or the feed rollers 32 and 33 are journaled for rotation within the housing 22 such that a portion of the roller is exposed to the exterior surface of the housing 22 for driving engagement with an output shaft of a motor or other device. For instance, the rollers may be mounted within the housing 22 similar to the rollers in a VCR tape. In a well-known VCR tape, the rollers are exposed through openings in the tape housing and include keyed receptacles for drivably receiving a drive shaft therein. It should be appreciated that the rollers may be disposed within the housing 22 in any suitable manner.

The dispensing cartridge 18 may further include first and second tension rollers 36 and 38 journaled for rotation within the housing 22 and positioned between the main roller 28 and the feed rollers 32 and 33. The tension rollers 36 and 38 are appropriately positioned and configured to keep tension in the HOA strip 26 as it passes over the tension rollers 36 and 38 towards the feed rollers 32 and 33. For instance, the HOA strip 26 may extend from the main roller 28 and pass beneath the first tension roller 36 and above the second tension roller 38 before reaching the feed rollers 32 and 33. The second tension roller 38 may be spring loaded and slidable within a slot 52 formed in the housing 22 to appropriately adjust the tension in the HOA strip 26. It should be appreciated that the dispensing cartridge 18 may instead be any other suitable design that is adapted to store and dispense the HOA dose packets 24 at the predetermined and designated HOA. Thus, the foregoing description should not be seen as limiting the scope of the present disclosure.

After loading the dispensing cartridge 18 with the HOA strip 26 and appropriately identifying the cartridge 18 and its contents with the GUI 56, the dispensing cartridges 18 are delivered to a patient's home 12 or other remote location for use with the dispenser 20. The pharmacy 10 may include a logistics system for delivering the dispensing cartridges 18 to a patient's home 12 or other remote location and loading the cartridges 18 into the dispenser 20 if needed. Instead, the patient can pick up the dispensing cartridges 18 at the pharmacy 10 or bring the dispenser 20 to the pharmacy 10 for refilling. Preferably, the opening 34 of the dispensing cartridge 18 is sealed with a tamper evident seal after being filled at the pharmacy 10 for secure shipping and to prevent any dirt, moisture, etc., from entering and contaminating the cartridge 18.

Referring to FIGS. 5 and 6, the dispensing cartridges 18 are loaded into the dispenser 20 located at the patient's home 12 for automatically dispensing each HOA dose packet 24 at the appropriate HOA. The dispenser 20 includes a housing 42 suitable for receiving at least one cartridge 18 therein. The dispensing cartridge 18 is loaded into the dispenser 20 by dropping or otherwise inserting the cartridge 18 into a load opening 48 defined in the housing 42. For instance, the dispenser 20 is shown in FIGS. 5 and 6 as having a side load opening 48 such that the dispensing cartridge 18 may be moved laterally into the dispenser 20. The dispenser 20 may instead include a load opening defined on the top of the dispenser housing 42 such that the cartridge may be dropped into the dispenser 20. A top load opening may be preferred if, for instance, the dispenser 20 was configured to received multiple dispensing cartridges.

The dispenser 20 is adapted to receive the dispensing cartridge 18 and mechanically engage the dispensing cartridge 18 without further effort. The dispenser 20 includes a motor 54 having an output shaft 56 that is engageable with one of the feed rollers 32 or 33 (or any other suitable roller) within the dispensing cartridge 18 to drive the HOA strip 26 toward an opening 30 in the dispenser 20 when it is the appropriate HOA. If the cartridge 18 is inserted laterally into the dispenser 20, the motor output shaft 56 is preferably directly engageable with one of the feed rollers 32 or 33 upon insertion into the dispenser 20. If it is preferred that the cartridge 18 be dropped down into the dispenser 20, the motor 54 may include an output drive shaft that is spring-loaded or otherwise selectively moveable within the dispenser 20 such that the output drive shaft is biased into mechanical, driving engagement with one of the rollers upon insertion of the cartridge 18 into the dispenser 20 but allows the cartridge 18 to pass over the output drive shaft when inserting the cartridge 18 into the dispenser 20, similar to that of a VCR or other known device. As such, when the cartridge 18 is inserted into the dispenser 20, the cartridge 18 is ready for dispensing.

The dispenser 20 will accept loading of separate dispensing cartridges 18, with each cartridge 18 including different types of HOA strips 26. As such, the dispenser 20 can accommodate several HOA dosing times during the day and can also accommodate special order (PRN) medications, short run doses, and new prescription doses. For instance, the dispenser 20 may receive three cartridges therein, with one cartridge containing a breakfast dose, a second cartridge containing a lunch dose, and a third cartridge containing a dinner dose. A fourth cartridge can be received within the dispenser for an optional bedtime dose, and a fifth cartridge can be used for newly added medications or individual medication courses.

The dispenser 20 may be any suitable design to accommodate numerous dispensing cartridges 18 for the patient. For instance, the dispenser 20 may be modular in design such that each modular unit includes a separate motor for engaging and driving the feed rollers 32 and 33 of the cartridge 18 disposed within that unit. In the alternative, the dispenser 20 may include only a single motor that is selectively engageable with each cartridge 18 at the appropriate HOA. Any dispenser design suitable for dispensing HOA dose packets 24 from each cartridge 18 at the appropriate HOA may instead be used.

The dispenser 20 may also include an opener (not shown) on the exterior of the dispenser that may be used to open the HOA dose packets 24 after they are dispensed. The opener is preferably a notch in the exterior of the dispenser 20 having a razor blade positioned to engage and open the HOA dose packets 24 as they are moved through the notch.

The dispenser may further include a display screen (not shown) suitable for communicating dosage information, alerts, errors, etc. to the patient as needed. The dispenser 20 may also include a local or remote audible, visual, and/or tactile alarm or other device for notifying the patient that an HOA dose packet 24 has been dispensed or that a message is on the display screen.

The dispenser 20 may be equipped with a secured wireless network device such as cellular broadband service. It can additionally or alternately be equipped with a secured Ethernet connection as well as a telephone jack as means of communication. This connection enables the dispenser 20 to communicate with the data center 14 to receive information such as updates, electronic manifests, schedules, and alerts. The dispenser 20 will also use this communication path to send out requests for replenishment or help or to communicate discrepancies in data or a change in data or schedules. The communication path may further provide the user with direct voice communication to contact support personnel when required. This communication path may also be utilized by other third party devices such non invasive blood pressure (NIBP) units or weight management systems.

The dispenser 20 includes a suitable controller 58 in operable communication with the components of the dispenser 20 and with the data center 14. More specifically, the controller 58 is in communication with the data center 14 for receiving and sending instructions from the data center 14 regarding dispensing, errors, inventory replenishment, etc. The controller 58 is also in communication with the motor 54 for actuating the motor 54 to engage a feed mechanism of a cartridge 18 to dispense an HOA dose packet 24 at the appropriate HOA. The controller 58 may further receive signals from various sensors located within the dispenser, such as a sensor for detecting whether an HOA dose packet 24 is ready and available for dispensing, a sensor for reading the GUI 56 on the cartridge, a sensor for detecting a missed HOA, etc. In response to such signals, the controller 58 can send signals to the data center 14, a third party, and/or to the display screen or alarm on the dispenser 20. Any suitable controller well known in the art may be used.

When the dispensing cartridge 18 is incorporated into the dispenser 20, it will be identified to the dispenser 20 by the globally unique identifier 56 on the dispensing cartridge 18. The identifier 56 will be cross referenced to the electronic manifest and schedule that was received from the data center 14. If the dispensing cartridge 18 cannot be matched to a manifest and schedule, the dispenser 20 sends a request to the data center 14 for the correct manifest and schedule. If the manifest and schedule are not available, the data center 14 will send an alert to a support system, and an error message is displayed on the dispenser screen. If the manifest and schedule are available, it will be communicated to the dispenser 20 and the motor 54 will engage one of the feed rollers 32 or 33 to place the first HOA dose packet 24 into a pre-staged position for delivery to the user. A sensor within the dispenser 20 near the opening 30 identifies the HOA dose packet 24 in the pre-stage position and verifies that the next packet is available.

The dispenser 20 will alert the patient when the HOA has arrived and an HOA dose packet 24 is available for retrieval. For instance, the dispenser 20 may sound a visual, audio, and/or tactile alarm to alert the user that the HOA dose packet 24 has been dispensed or is ready for dispensing. The dispenser 20 may also send a wireless signal to a receiver that is enclosed in a wearable apparatus worn by the patient, such as a pager, jewelry, or other accessories. The signal may also be sent to a patient's email, a cell phone (call or text), a land line phone, etc. The dispenser 20 may also include multiple levels of alarms (such as a local alarm on the dispensing system followed by an alarm on a cell phone). The actual announcement may vary from a vibration to a beep or a combination of both, as well as escalations in tone or vibration as time passes. Additionally, the alarm type may be modified to accommodate persons of varying disability, e.g., a flashing strobe or light in the absence of an auditory alarm for persons of hearing disability.

The patient may be required to supply proof of identification (biometrics scan or a personal identification number) or proof of presence before the HOA dose packet 24 is dispensed. After verification of the correct patient or presence of the patient, the dispenser 20 will present the sealed HOA dose packet 24 or packets to the patient.

Should the correct patient fail to be identified in a predetermined time frame, the dispenser will not eject the HOA dose packet 24. Rather, the HOA dose packet 24 can remain in the pre-staged position until the HOA reoccurs. Because the medications are stored in HOA specific packaging, the dose can be dispensed at the next HOA. The missed HOA dose packet 24 may instead be stored in an internal chamber 40 within a front portion of the dispenser 20. The chamber 40 could include an internal hinged door 44 that opens for retrieval of the missed HOA dose packet 24 when the packet cannot be ejected. At the same time, the opening 30 of the dispenser may be closed by the controller 58 to either prevent an unauthorized user from accessing the missed HOA dose packet 24 or to prevent the correct user from accessing the packet after the HOA occurs. The patient or caregiver may access the missed packets through a secured access door (not shown) that opens to the chamber 40.

If the patient fails to retrieve the medication at the HOA, the controller 58 will run an internal protocol for a missed medication and send the appropriate signals to the data center 14 or another location. The protocol may include contacting a predetermined contact person, holding the missed dose, logging information for later review by prescribing physician, etc. This protocol may be determined by the prescribing doctor. The controller 58 may send appropriate signals to carry out the protocol over a hardwired phone line using a secured protocol over a wired or wireless connection.

If a mechanical failure occurs and the dispenser 20 fails to dispense the HOA dose packet 24 at the HOA, the patient can remove the dispensing cartridge 18 from the dispenser 20 and open the dispensing cartridge 18 with a key or other secure device. As such, the patient can remove the HOA dose packets 24 from the dispensing cartridge 18 and take the medications as instructed on the packets.

While the preferred embodiment of the present disclosure has been illustrated and described, it will be appreciated that various changes can be made therein without departing from the spirit and scope of the present disclosure.

The embodiments of the present disclosure in which an exclusive property or privilege is claimed are defined as follows:

1. A remote pharmaceutical dispensing system for automatically dispensing medication, comprising:
   (a) a plurality of packets each containing at least one type of medication for a predetermined hour of administration;
   (b) at least one cartridge having a cartridge housing with an interior and a cover for selectively enclosing contents within the interior of the cartridge housing, the cover securable to the cartridge housing in a locked position, wherein the cover securely encloses the contents within the interior of the cartridge housing to substantially prevent access to the contents, and an unlocked position, wherein the cover is at least partially removable from the cartridge housing to allow access to the contents within the interior of the cartridge housing;
   (c) a feed mechanism disposed within the interior of the cartridge housing, the feed mechanism suitable for advancing at least one of the plurality of packets containing at least one type of medication through an opening in the cartridge housing;
   (d) a dispenser having a dispenser housing sized and configured to receive the at least one cartridge, the dispenser housing having an opening in substantial alignment with the opening in the cartridge housing, the dispenser further including a motor that is drivably engageable with the feed mechanism of the cartridge when the cartridge is inserted into the dispenser to advance the at least one of the plurality of packets containing at least one type of medication through the opening in the cartridge housing and through the opening in the dispenser housing, the motor drivably engageable with the feed mechanism when the cover is secured to the cartridge housing in the locked position; and
   (e) a controller in operable communication with the motor and configured to actuate the motor to advance at least one of the plurality of packets containing at least one type of medication through the opening in the cartridge housing and through the opening in the dispenser housing at the predetermined hour of administration.

2. The system of claim 1, wherein the controller is in networked communication with a data center and a pharmacy.

3. The system of claim 2, wherein the data center is configured to receive instructions from the pharmacy and communicate with the controller for instructing the controller to actuate the motor to advance at least one of the plurality of packets containing at least one type of medication through the opening in the cartridge housing and through the opening in the dispenser housing at the predetermined hour of administration based upon the instructions received from the pharmacy.

4. The system of claim 3, wherein the cartridge includes a unique identifier that is identifiable by the controller when the cartridge is received within the dispenser, and wherein the controller sends the unique identifier to the data center.

5. The system of claim 4, wherein the data center sends unique dispensing instructions to the controller corresponding to the cartridge received within the dispenser.

6. The system of claim 5, wherein the pharmacy includes a pharmacy information system having software that is capable of receiving and processing prescriptions sent from the data center.

7. The system of claim 6, wherein the software creates an electronic manifest corresponding to each unique identifier, the electronic manifest containing a record of the plurality of packets, the at least one type of medication contained within the plurality of packets, and the hour of administration for each of the plurality of packets, and wherein the electronic manifest is sent to the controller through the data center.

8. The system of claim 2, wherein the data center communicates with the controller for monitoring the inventory of the plurality of packets each containing at least one type of medication within the dispenser.

9. The system of claim 1, wherein the plurality of packets each containing at least one type of medication are secured to one another end to end to define a strip, and wherein a transverse perforation is defined between each of the plurality of packets such that the plurality of packets are separable from one another.

10. The system of claim 1, wherein each of the plurality of packets is labeled with information suitable for uniquely identifying at least one type of medication contained within the packet.

11. The system of claim 1, wherein each of the plurality of packets contains more than one type of medication for a predetermined hour of administration.

12. A remote pharmaceutical dispensing system for automatically dispensing medication, comprising:
   (a) a plurality of packets, at least some of the plurality of packets containing at least one type of medication for a predetermined hour of administration;
   (b) at least one cartridge having a cartridge housing with an interior and a cover for selectively enclosing contents within the interior of the cartridge housing, the cover securable to the cartridge housing in a locked position, wherein the cover securely encloses the contents within the interior of the cartridge housing to substantially prevent access to the contents, and an unlocked position, wherein the cover is at least partially removable from the cartridge housing to allow access to the contents within the interior of the cartridge housing;
   (c) a feed mechanism disposed within the interior of the cartridge housing, the feed mechanism suitable for advancing at least one of the plurality of packets containing at least one type of medication through an opening in the cartridge housing;
   (d) a dispenser having a dispenser housing sized and configured to receive the at least one cartridge, the dispenser housing having an opening in substantial alignment with the opening in the cartridge housing, the dispenser further including a motor that is drivably engageable with the feed mechanism of the cartridge when the cartridge is inserted into the dispenser to advance the at least one of the plurality of packets containing at least one type of medication through the opening in the cartridge housing and through the opening in the dispenser housing, the motor drivably engageable with the feed mechanism when the cover is secured to the cartridge housing in the locked position; and (e) a controller in operable communication with the motor and configured to actuate the motor to advance at least one of the plurality of packets containing at least one type of medication through the opening in the cartridge housing and through the opening in the dispenser housing at the predetermined hour of administration.

* * * * *